United States Patent
Buchok et al.

(10) Patent No.: US 8,096,945 B2
(45) Date of Patent: Jan. 17, 2012

(54) DISPOSABLE SPECULUMS HAVING SINGLE-SIDED SUPPORT AND OPERATING MECHANISM

(75) Inventors: Aaron J. Buchok, Arlington, TX (US); Jeffrey R. Swift, Boca Grande, FL (US)

(73) Assignee: OBP Corporation, Lawrence, MA (US)

( * ) Notice: Subject to any disclaimer, the term of this patent is extended or adjusted under 35 U.S.C. 154(b) by 213 days.

(21) Appl. No.: 12/478,339

(22) Filed: Jun. 4, 2009

(65) Prior Publication Data
US 2009/0312610 A1    Dec. 17, 2009

Related U.S. Application Data

(60) Provisional application No. 61/061,368, filed on Jun. 13, 2008.

(51) Int. Cl.
*A61B 1/32* (2006.01)
(52) U.S. Cl. ........................ 600/205; 600/220
(58) Field of Classification Search ........... 600/184–246
See application file for complete search history.

(56) References Cited

U.S. PATENT DOCUMENTS

| | | |
|---|---|---|
| 3,851,642 A | 12/1974 | McDonald |
| 3,985,125 A | 10/1976 | Rose |
| 4,597,383 A | 7/1986 | VanDerBel |
| 4,766,887 A | 8/1988 | Cecil, Jr. et al. |
| 4,966,130 A | 10/1990 | Montaldi |
| 4,971,036 A | 11/1990 | Collins |
| 5,018,507 A | 5/1991 | Montaldi |
| 5,179,938 A | 1/1993 | Lonky |
| 5,231,973 A | 8/1993 | Dickie |
| 5,465,709 A | 11/1995 | Dickie et al. |
| 5,499,964 A | 3/1996 | Beck et al. |
| 6,048,308 A | 4/2000 | Strong |
| 6,280,379 B1 * | 8/2001 | Resnick ............... 600/220 |
| 6,379,299 B1 | 4/2002 | Borodulin et al. |
| 6,450,952 B1 | 9/2002 | Rioux et al. |
| 6,569,091 B2 | 5/2003 | Diokno et al. |
| 6,595,917 B2 | 7/2003 | Nieto |
| 6,702,741 B2 | 3/2004 | Rioux et al. |
| 6,712,761 B2 | 3/2004 | Borodulin et al. |
| 6,740,031 B2 | 5/2004 | Davidson et al. |
| 7,311,663 B2 | 12/2007 | Marcotte |
| 7,371,212 B2 | 5/2008 | Klaassen |
| 2002/0156350 A1 | 10/2002 | Nieto |
| 2003/0095781 A1 * | 5/2003 | Williams ............... 385/146 |
| 2003/0176772 A1 | 9/2003 | Yang |
| 2007/0156022 A1 | 7/2007 | Patel |
| 2007/0230164 A1 | 10/2007 | Vivenzio et al. |
| 2007/0230167 A1 | 10/2007 | McMahon et al. |
| 2007/0255110 A1 | 11/2007 | Wax et al. |
| 2009/0097236 A1 * | 4/2009 | Miller et al. ............ 362/119 |

* cited by examiner

*Primary Examiner* — Eduardo C Robert
*Assistant Examiner* — Summer Kostelnik
(74) *Attorney, Agent, or Firm* — Bowditch & Dewey, LLP

(57) ABSTRACT

The embodiments disclosed herein relate to disposable speculums, and more particularly to disposable vaginal speculums having single-sided support and operating mechanisms. In an embodiment, a speculum includes an upper member having an upper blade and a hinge assembly; a lower member having a handle and a lower blade, wherein a combined smoke channel light guide directs light from a light source in the handle to a distal end of the lower blade for smoke removal; and a linear support member having a proximal end, a distal end, and an elongated body therebetween, the linear support member vertically moveable within a track positioned in the lower member.

20 Claims, 14 Drawing Sheets

130

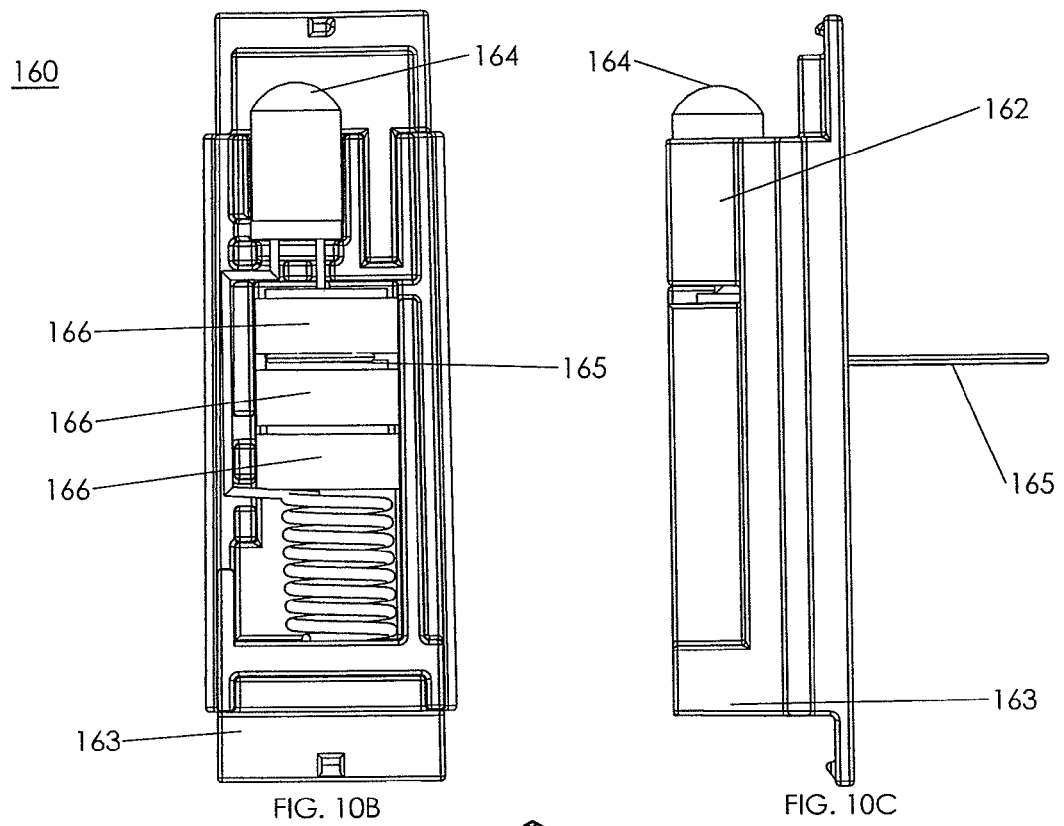
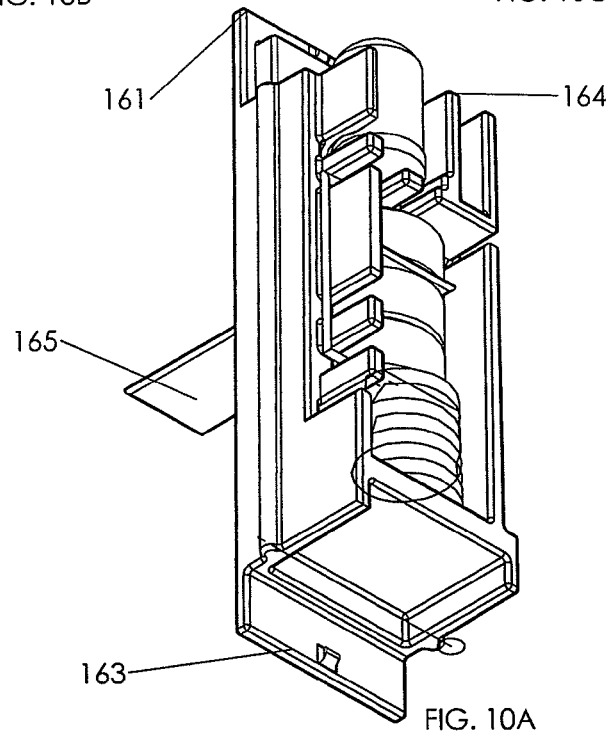
FIG. 10B  FIG. 10C
FIG. 10A

DISPOSABLE SPECULUMS HAVING SINGLE-SIDED SUPPORT AND OPERATING MECHANISM

RELATED APPLICATIONS

This application is related to and claims the benefit of priority from U.S. Provisional Patent Application No. 61/061,368, filed on Jun. 13, 2008, the entirety of which is incorporated herein by reference.

FIELD

The embodiments disclosed herein relate to speculums, and more particularly to disposable vaginal speculums having single-sided support and operating mechanisms.

BACKGROUND

A speculum is a medical instrument for dilating the opening of a body cavity for medical examination. A vaginal speculum commonly used during a gynecological examination or a surgical procedure is introduced into a patient's vagina to separate the vaginal walls, thus allowing the internal genital organs to be examined. Metal, autoclavable duck-bill specula are conventionally used for gynecological examination and treatment. These units, with exposed joints, sharp edges, and cold metal are universally disliked by patients. The hinged joints and blade edges often pinch, scrape, or otherwise traumatize the supporting tissues in the area being examined. The conventional metallic specula blades are typically opaque, therefore the only area available for inspection when a metallic speculum is in use is the open end, for cervical examination, and the vaginal wall areas between the blades.

In an attempt to eliminate some of the problems mentioned above, plastic specula have been developed. The plastic specula, which are formed from plastic or another lightweight and inexpensive material are often designed with a double-hinge. This is because the lightweight and inexpensive material from which the speculum hinge is formed is unable to support the oblique stress caused by external, vaginal pressure on a single-hinged speculum. This double-hinge design results in a closed speculum design, which makes it difficult for the professional to manipulate instruments, such as scissors, forceps and probes that are commonly used in conjunction with the speculum, and vacuum instruments that are needed to evacuate debris and bodily fluids. Also, this double-hinge can obstruct the professional's vision of the genital tract, and makes it difficult to remove the speculum while other instruments remain inserted into the vagina.

Sufficient lighting of the subject area for examination is another area of difficulty, since typical specula are not equipped with illumination devices. Light must be directed from another source, often a gooseneck lamp that can partially obstruct the view into the vagina. Head mounted lights have been used as a partial solution to this problem, but mounted lights are uncomfortable for the operator and cumbersome due to the light cord.

SUMMARY

According to aspects illustrated herein, there is provided a speculum that includes a linear support member having a proximal end, a distal end, and an elongated body therebetween, the proximal end of the linear support member positioned within a space defined between two parallel pieces extending downward from an interior side of a hinge assembly, the hinge assembly positioned at a single side of an upper blade of the speculum, the elongated body of the linear support member vertically moveable within a track positioned at a single side of a handle portion of a lower member of the speculum.

According to aspects illustrated herein, there is provided a speculum that includes an upper member having an upper blade and a hinge assembly; a lower member having a handle and a lower blade, wherein a combined smoke channel light guide directs light from a light source in the handle to a distal end of the lower blade for smoke removal; and a linear support member having a proximal end, a distal end, and an elongated body therebetween, the linear support member vertically moveable within a track in the handle of the lower member.

According to aspects illustrated herein, there is provided a method for dilating a vagina that includes providing a disposable vaginal speculum, the speculum having an upper member having an upper blade; a support structure including a pair of parallel pieces spaced a distance apart that extend downward from an interior side of the upper blade; an operating mechanism extending off from the support structure and including an operating arm, the operating mechanism positioned at a single side of the upper blade; a lower member having a lower blade; and a linear support member having a proximal end, a distal end, and an elongated body therebetween, the linear support member vertically moveable within a track positioned at a single side of a handle portion of the lower member; inserting the upper blade and the lower blade of the speculum into an opening of the vagina; and creating a working space between the upper blade and the lower blade, thus dilating the vagina.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A is a perspective view of the vaginal speculum. FIG. 1B is a rear view of the vaginal speculum.

FIG. 4A is a rear perspective view of the lower member. FIG. 4B is a front perspective view of the lower member.

FIG. 8A is a side view of the upper member secured to the linear support member. FIG. 8B is a perspective view of the upper member secured to the linear support member.

FIG. 10A, FIG. 10B and FIG. 10C show an embodiment of a light source for use with the vaginal speculum of FIG. 1A and FIG. 1B. FIG. 10A is a perspective view of the light source showing some of the outer and the inner components. FIG. 10B is a back view of the light source showing inner components. FIG. 10C is a side view of the light source showing some of the outer components.

Figure 1A:
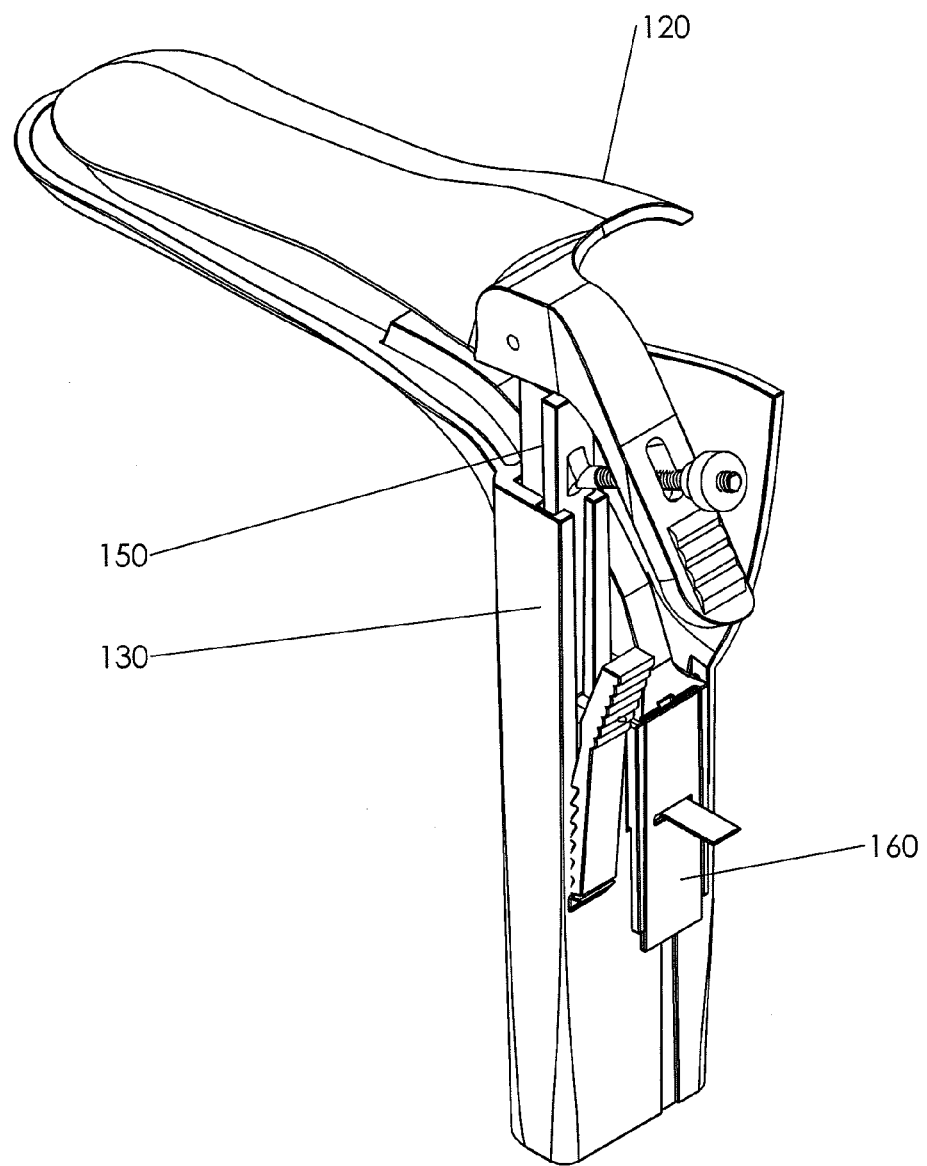
FIG. 1A and FIG. 1B show an embodiment of a vaginal speculum of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Vaginal speculums having single-sided support and operating mechanisms are disclosed herein. The disclosed vaginal speculums are fabricated from plastic materials, and are designed to be for single-use and are fully disposable. Although the vaginal speculums disclosed herein are intended to be used by gynecologists, it is understood that the vaginal speculums may also be used for example, by primary care physicians, geriatricians, urologists and nurse practitioners.

As used herein, the term "cross-contamination" refers to the passing of bacteria or viruses indirectly from one patient to another through the use of improper sterilization procedures, unclean instruments, or recycling of products.

As used herein, the term "disposable" refers to a vaginal speculum of the present disclosure designed for short-term convenience, and intended for single-use. The disposable vaginal speculum therefore do not need to be sterilized after use, which reduces the cost of maintaining the vaginal speculum, and minimizes the risk of cross-contamination.

As used herein, the term "female internal genital organs" refers to the vulva, vagina and cervix.

As used herein, the term "gynecological examination" or "surgical procedure" refers to a medical procedure performed on a female patient to visualize, inspect, and/or remove a portion of the female internal genital organs. Common gynecological procedures and surgeries include, but are not limited to, colposcopy, cervical cryosurgery, loop electrosurgical excision procedure (LEEP) procedure, hysteroscopy, dilation and curettage (D&C), cervical biopsy, transcervical chorionic villus sampling, endometrial ablation, endometrial biopsy, vaginal hysterectomy and PAP test. The vaginal speculums disclosed herein can be used during various medical procedures, and more particularly are used for gynecological procedures either in an office or hospital setting.

As used herein, the term "elevational movement" refers to the vertical up-and-down movement of an upper blade relative to a lower blade of a vaginal speculum of the present disclosure.

As used herein, the term "linear" refers to a straight line of material, for example, a straight line of plastic material. A linear support member refers to a support member of the present disclosure that is made from a straight line of plastic material, having no curves or angles.

As used herein, the term "angulational movement" refers to the angular up-and-down movement of an upper blade relative to a lower blade of a vaginal speculum of the present disclosure.

As used herein, the term "open state" refers to the positioning of an upper blade and a lower blade of a vaginal speculum of the present disclosure at a spaced-apart distance. The open state may be accomplished by elevating a support member that connects the upper blade and the lower blade together, by angularly moving the upper blade relative to the lower blade, or by a combination of both.

As used herein, the term "working space" refers to a space created between an upper blade and a lower blade of a speculum of the present disclosure. In an embodiment, the working space is created for viewing, examining, and performing surgical procedures on female internal genital organs.

As used herein, the term "structural integrity" refers to a feature provided by a vaginal speculum of the present disclosure prior to, during, and after use. An upper blade and a lower blade of the speculum are designed to withstand applied loads and transfer these applied loads to various other components of the speculum, while maintaining the structural integrity of the speculum.

As used herein, the term "fulcrum" refers to a support structure created by engaging a support member and a support structure of a vaginal speculum of the present disclosure. The created fulcrum results in the ability of an upper blade of the vaginal speculum to angularly move with relation to a lower blade of the vaginal speculum.

Figure 1B:
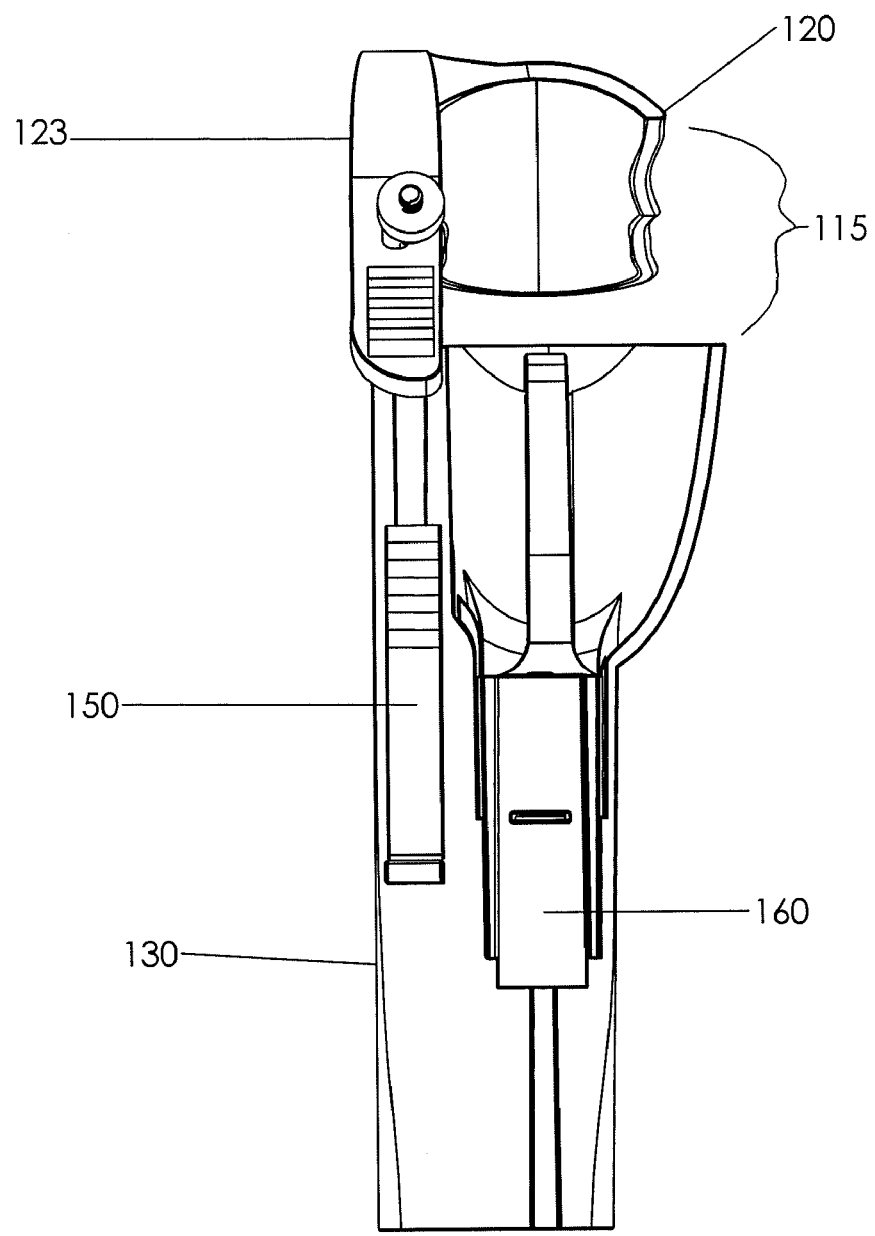

As shown in FIG. 1A and FIG. 1B, a disposable vaginal speculum 100 of the present disclosure includes an upper member 120, a linear support member 150, and a lower member 130 having a built-in light source 160. The linear support member 150 is engaged to both the upper member 120 and the lower member 130, as will be described in detail below. Unlike metallic speculum, which are not designed for single-use but instead are meant to be re-used many times with sterilization occurring between each use, the entire speculum 100 of the presently disclosed embodiments is fabricated from one or more plastics or plastic composites, sterilized when manufactured or packaged, and sufficiently inexpensive to be discarded after only one use. Sterilization of reusable specula can be costly and time-consuming. More significantly, if sterilization is not done properly, blood borne pathogens or other harmful biological agents from one patient can survive the sterilization process and be transmitted to another patient. Because the entire speculum 100 of the presently disclosed embodiments is disposable, there is no need to sterilize the speculum 100 after each use, which greatly reduces the time and cost associated with such sterilization procedures and prevents cross-contamination. Exemplary plastic materials which may be used to construct the various components of the speculum 100 include, but are not limited to, polypropylene, polyester, polyethylene, acrylic, polycarbonate, polyamide, polystyrene, and any composite of more than one of these plastics.

In an embodiment, the upper member 120 and the lower member 130 are fabricated from plastic materials that are substantially rigid and capable of transmitting light. For example, the upper member 120 and the lower member 130 may be molded from a colorless transparent plastic material such as acrylic plastic or the like. Acrylic plastic is relatively rigid, can be injection molded or extruded, and has excellent light conductive properties most suitable for use with the speculum 100 of the present disclosure. In an embodiment, the linear support member 150 is fabricated from a different plastic material than the upper member 120 and the lower member 130. The linear support member 150 is fabricated from a rigid, sturdy, plastic material that can handle various load patterns, as will be described in detail below. In an embodiment, the upper member 120 and the lower member 130 are fabricated from a polycarbonate material. In an embodiment, the linear support member 150 is fabricated from a polyester material. In an embodiment, the linear support member 150 is fabricated from a polyamide material, for example, nylon.

Figure 2:
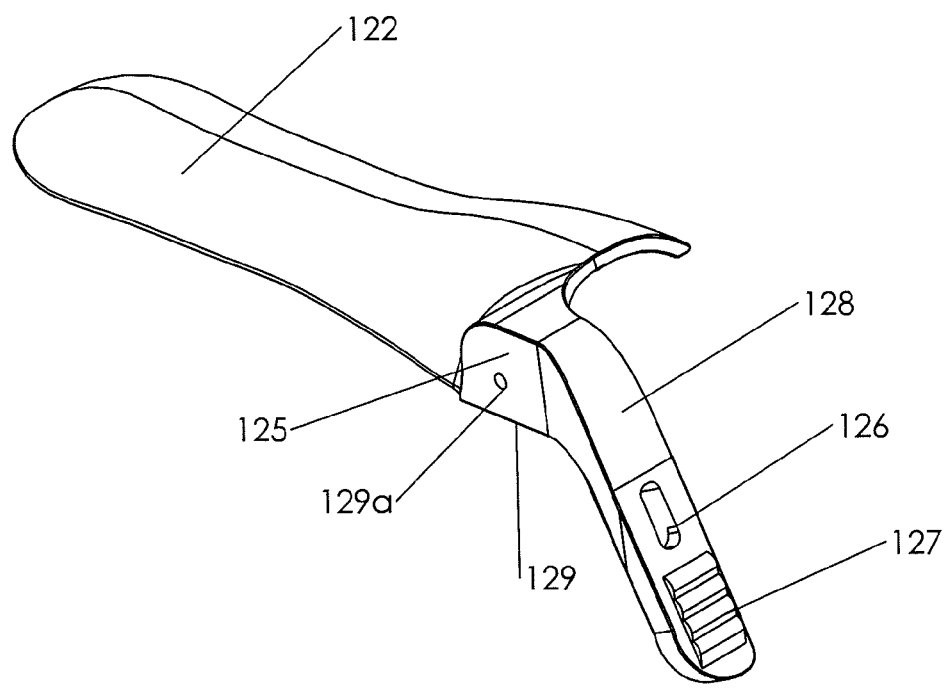
FIG. 2 is a perspective view of an upper member of the vaginal speculum of FIG. A.

As best illustrated in FIG. 2, the disposable speculum 100 comprises an upper member 120 having an upper blade 122 that terminates in a hinge assembly 125. The hinge assembly 125 receives and transfers loads placed on the upper member 120 and the lower member 130 to various components of the speculum 100, as will be described in detail below. The hinge assembly 125 includes an operating mechanism 128 which extends out from the hinge assembly 125. As shown in the embodiments depicted in the figures, the operating mechanism 128 is located on a left-side of the upper blade 122. In another embodiment, the operating mechanism 128 may be located on a right-side of the upper blade 122. The unique design and low profile of the hinge assembly 125 enable a user of the speculum 100 to have a large unobstructed view of a patient during a gynecological procedure. In an embodiment, the operating mechanism 128 extends out and down from the upper blade 122 at an angle. Also, a working space 115 created when the speculum 100 is in an open state (see FIG. 1B, the speculum 100 is not shown entirely in the open state in the figures) provides exceptional instrument maneuverability to the user of the speculum 100. The speculums known in the art often provide a limited working space with limited visibility due to a poorly designed hinge assembly. The working space 115 also uniquely allows for the removal of the speculum 100 from the vagina while other procedural instruments remain inserted in the vaginal cavity.

Figure 3:
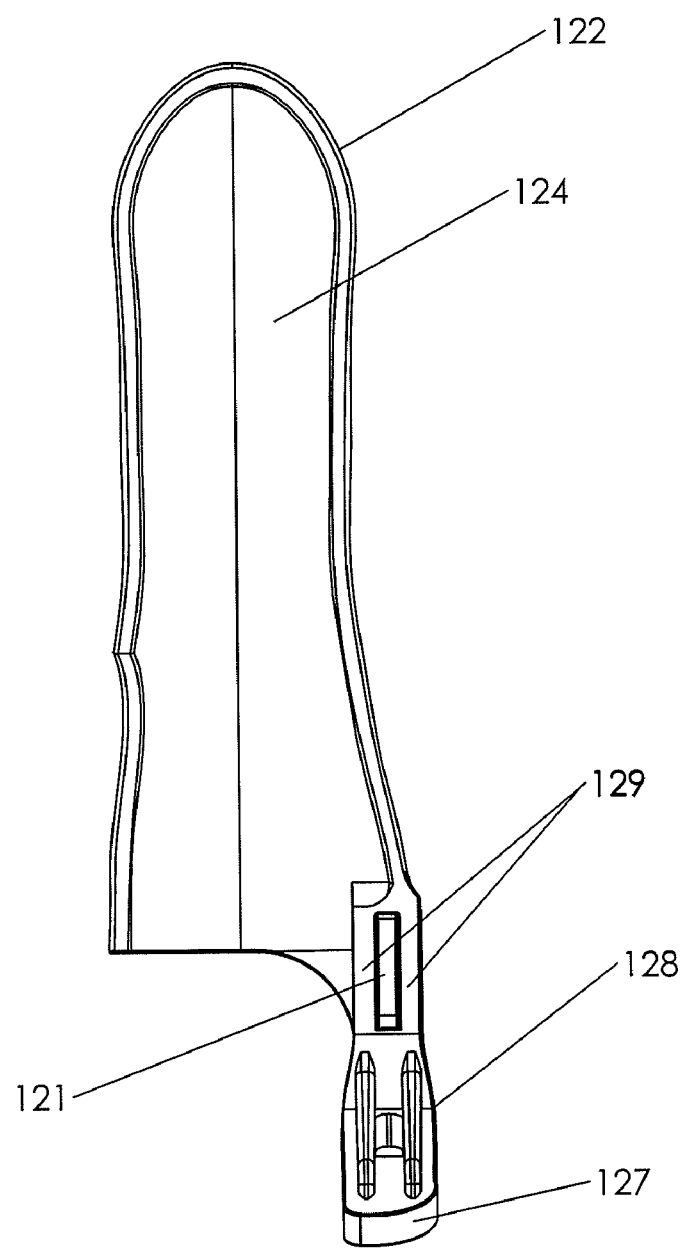
FIG. 3 is a plan view showing an interior side of the upper member of the vaginal speculum of FIG. 2. The upper member includes an upper blade, a supporting structure, and an operating mechanism.

As shown in FIG. 2 and FIG. 3, the hinge assembly 125 comprises a pair of parallel support beams or pieces 129 spaced a distance apart, each having an opening 129a. An opening 121 is created by the spacing of the pair of parallel support beams 129. In an embodiment, the parallel support beams 129 are spaced apart at a distance that ranges from about 3/32 inches apart to about 1/8 inches apart. The pair of parallel support beams 129 extend down from an interior side 124 of the upper blade 122. The operating mechanism 128 includes an operating arm 127 which allows a user of the speculum 100 to move the upper blade 122 at various angles when pressure is applied to the operating arm 127 during use of the speculum 100, and an opening 126 for which an angulation arm of the linear support member 150 moves through and locks with. The upper blade 122 has a thickness, a width and a curve, which prevents failure of the upper blade 122 with the application of pressure or stress, for example during a gynecological procedure. In an embodiment, the upper blade 122 has a rounded distal end.

Figure 4A:
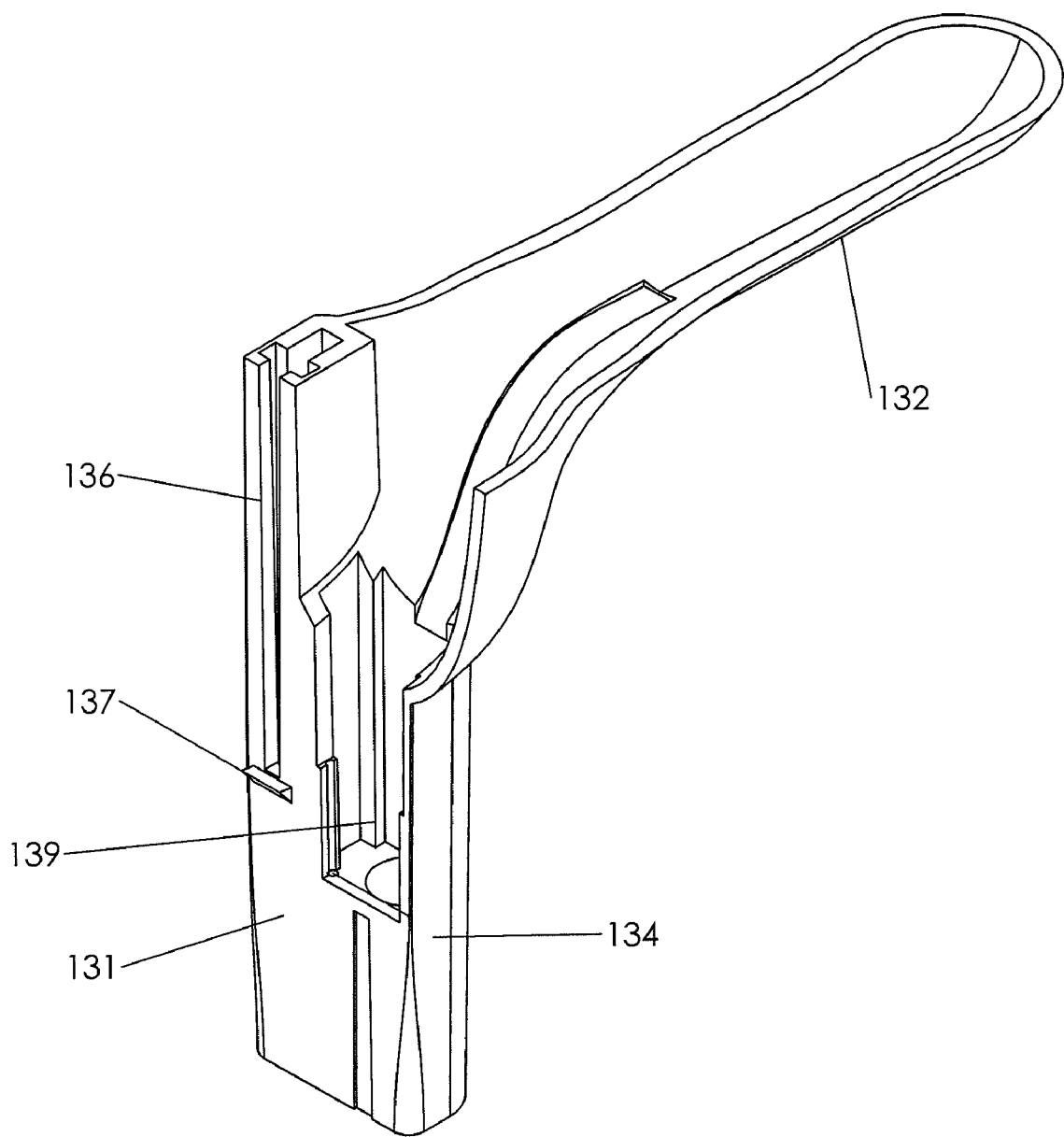
FIG. 4A and FIG. 4B are perspective views of a lower member of the vaginal speculum of FIG. 1A.
Figure 4B:
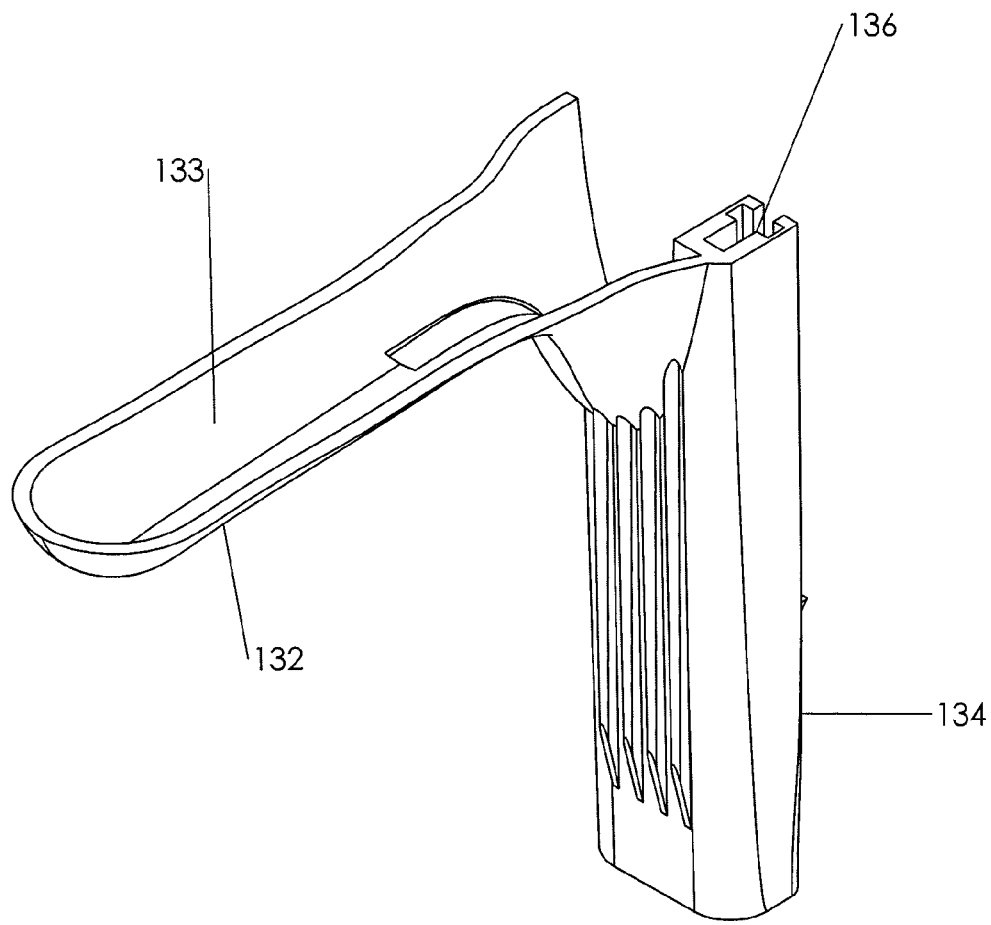

FIG. 4A and FIG. 4B show the lower member 130 of the speculum 100. The lower member 130 includes a lower blade 132 and a handle portion 134. The handle portion 134 includes a vertical track 136 for elevational movement of the linear support member 150, and a location for an internally powered built-in light source housed within a cavity 139. In an embodiment, the track 136 is a carved-out space positioned at a single side of the handle portion 134. On an outer surface 131 of the handle 134 at a distal end of the track 136, there is a stop tab 137. The stop tab 137 encounters locking teeth on an elevation leg of the linear support member 150 and maintains the speculum 100 in an open state at various, user selected distances. A sunken-relief 135 is sufficiently designed to accept a smoke channel light guide as described below. As shown in the embodiment depicted in FIG. 4B, the handle 134 has at least one shaped surface so that a user of the speculum 100 may easily grasp the handle 134. The lower blade 132 has a thickness, a width, and a curve which prevents failure of the blade 132 with the application of pressure or stress. In an embodiment, the lower blade 132 has a rounded distal end.

Figure 5:
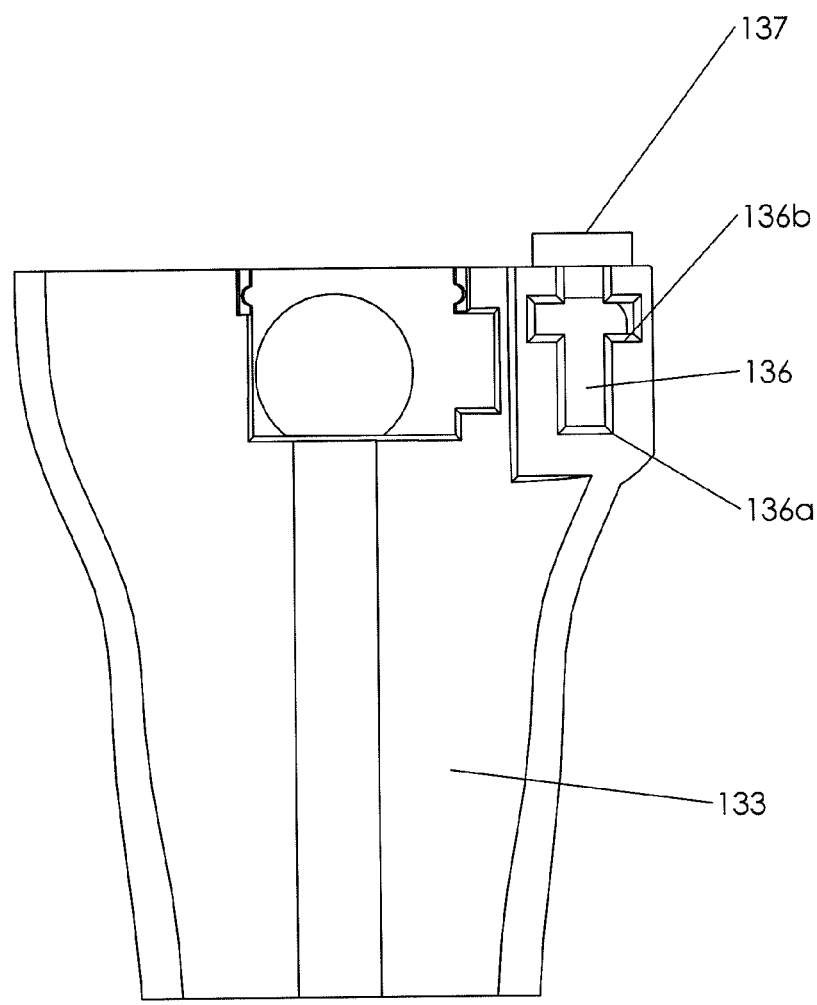
FIG. 5 is a close-up plan view of the lower member of the vaginal speculum of FIG. 4A and FIG. 4B. The lower member includes a lower blade and a track for engaging a linear support member.
Figure 6:
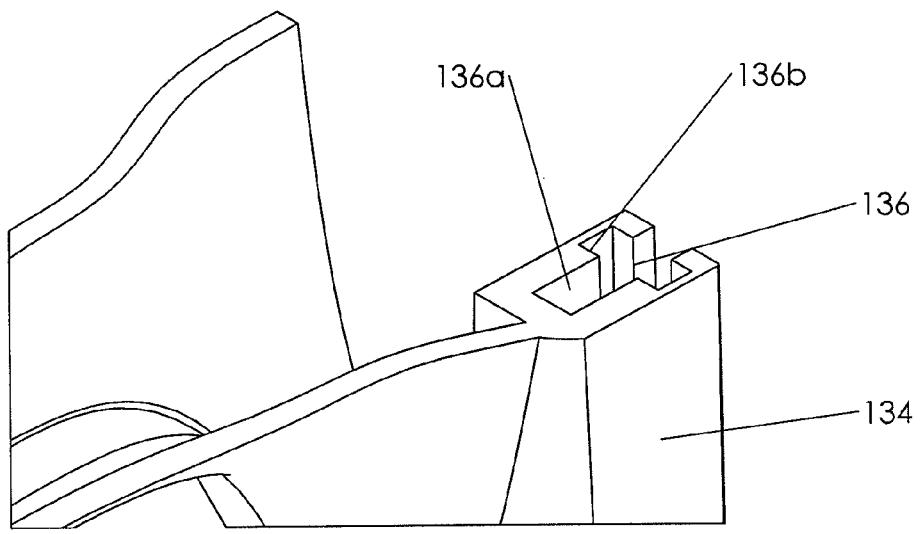
FIG. 6 is a close-up perspective view of the track of FIG. 5.

FIG. 5 shows a close-up plan view showing an interior surface 133 of the lower blade 132. The track 136 has a "T-shape", with a long vertical section represented by 136a and a shorter horizontal section represented by 136b for accepting the linear support member 150. FIG. 6 shows a close-up perspective view of the track 136 in which the support member 150 rides in.

Figure 7:
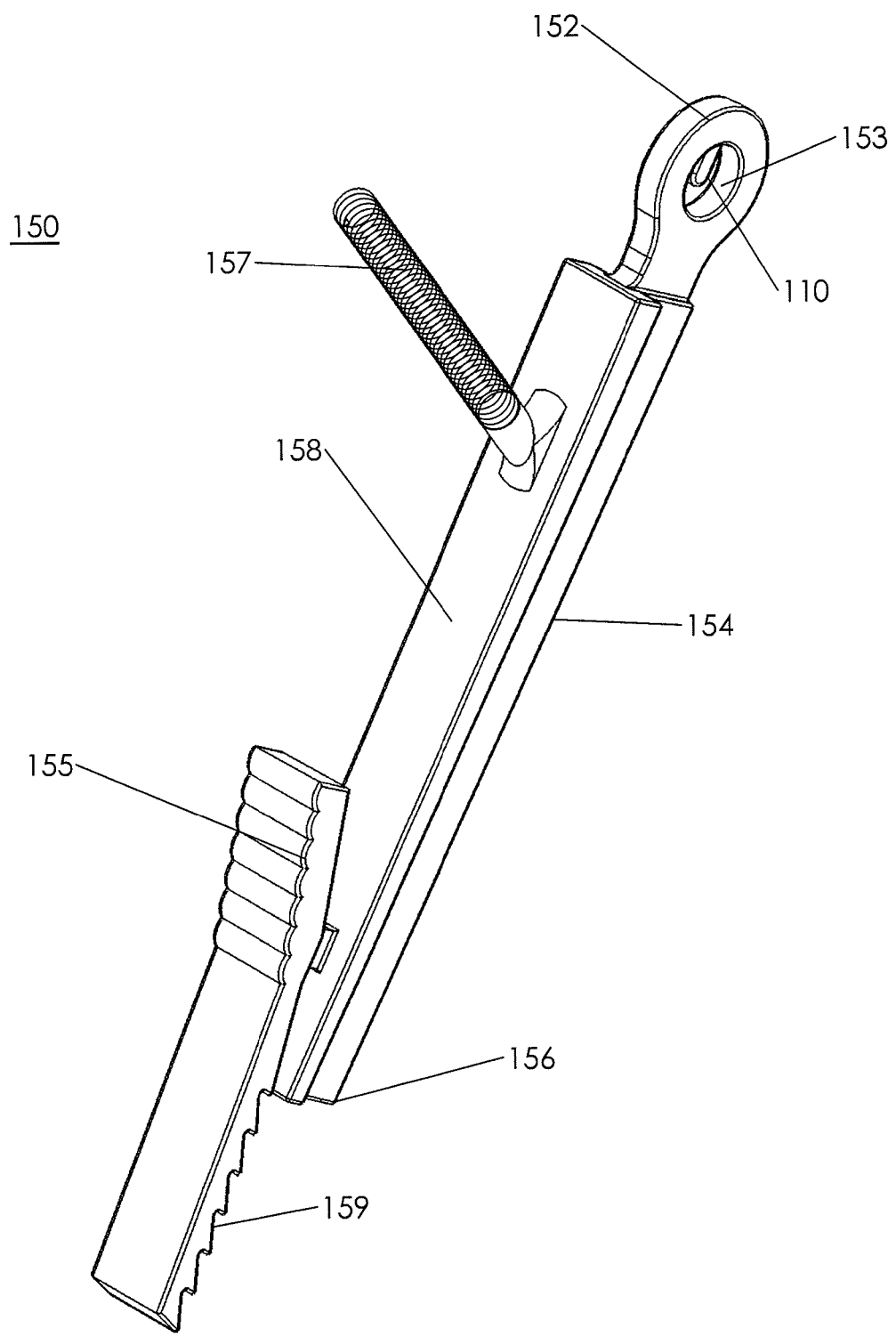
FIG. 7 is a perspective view of a linear support member of the vaginal speculum of FIG. 1A and FIG. B.
Figure 8A:
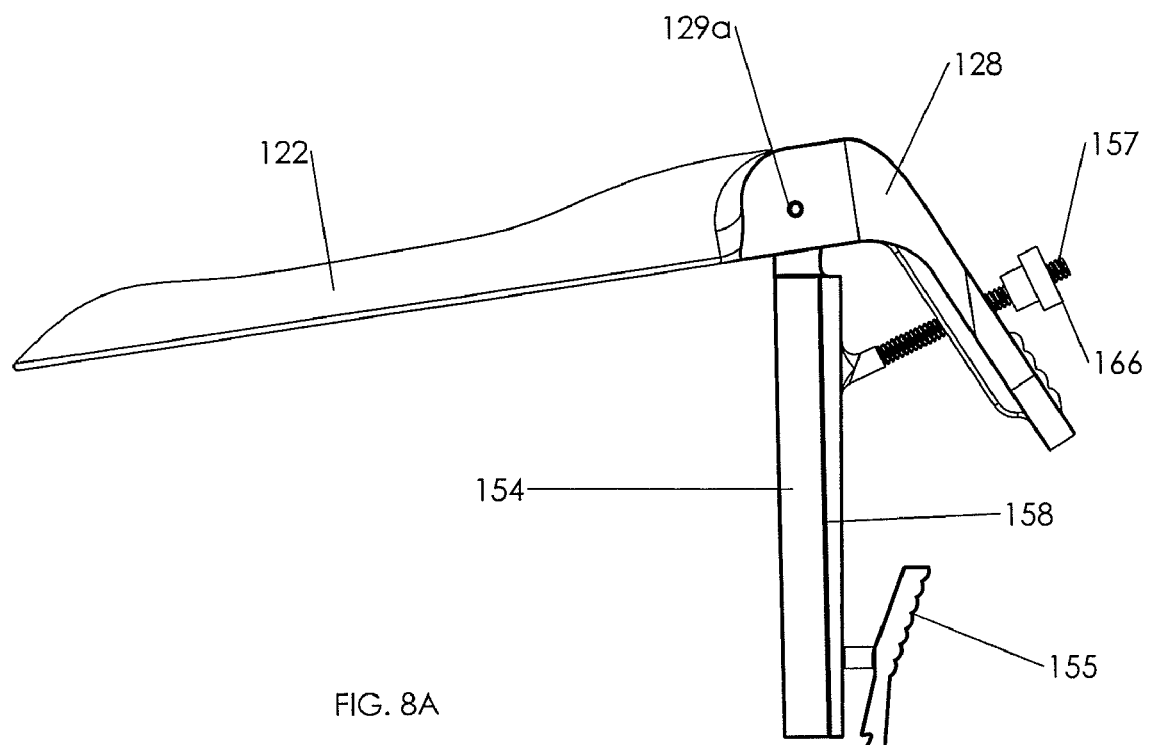
FIG. 8A and FIG. 8B show the upper member of FIG. 1A and FIG. 1B secured to the linear support member of FIG. 7.
Figure 8B:
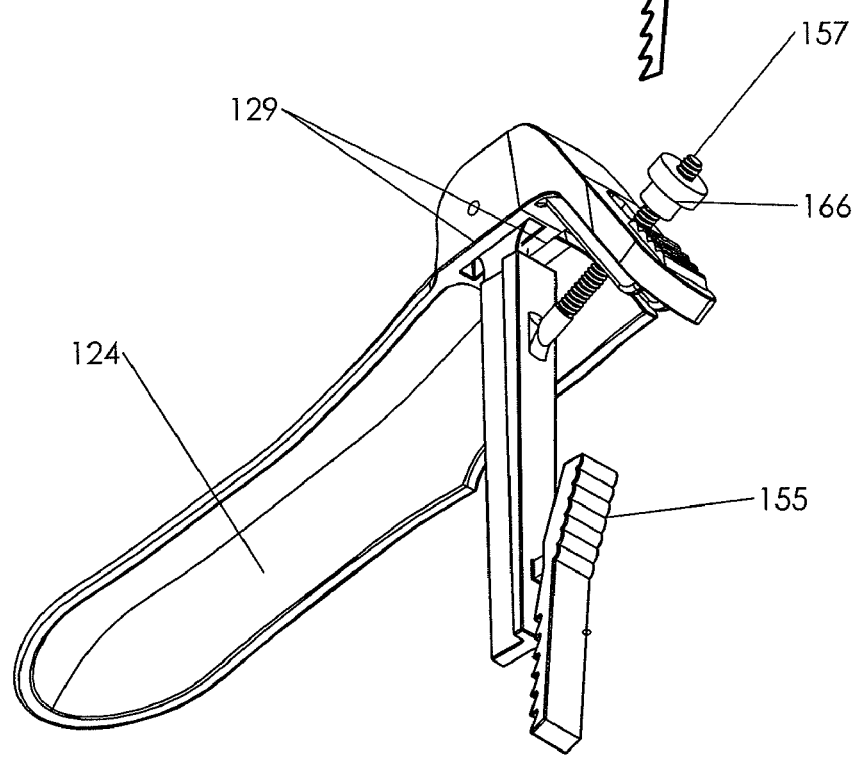
Figure 9:
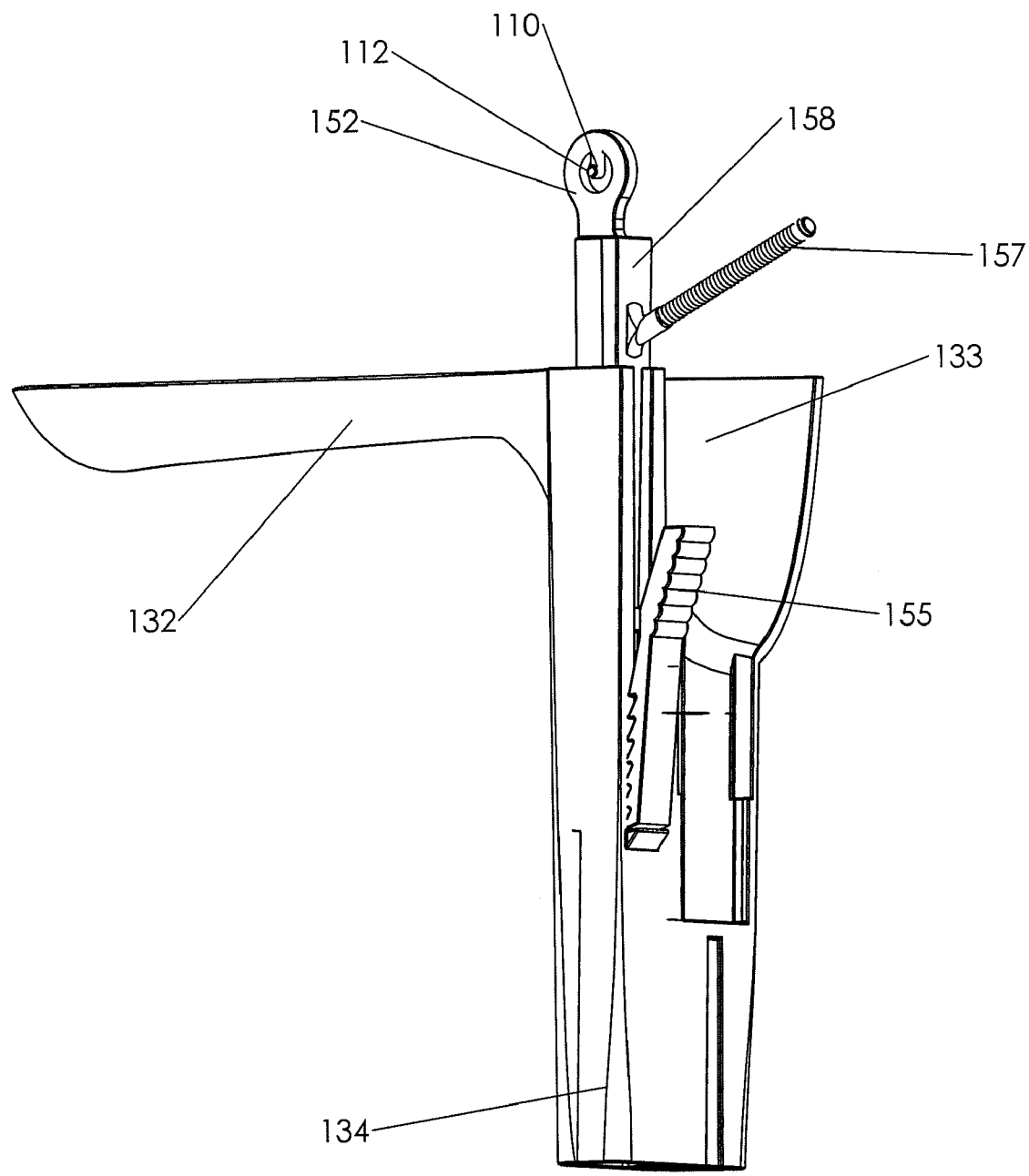
FIG. 9 is a perspective rear view of the linear support member of FIG. 7 positioned within the track of the lower member of FIG. 6.

FIG. 7 in conjunction with FIG. 8A, FIG. 8B and FIG. 9, show various views of the linear support member 150 of the vaginal speculum 100. The linear support member 150 has a proximal end 152, a distal end 156 and an elongated body 154 having a "T-shape". The elongated body 154 rides within the track 136. The proximal end 152 of the linear support member 150 attaches with the hinge assembly 125 of the upper member 120. The proximal end 152 of the linear support member 150 fits within the space 121 between the pair of parallel support beams 129 of the hinge assembly 125, such that the pair of parallel support beams 129 surround the linear support member 150. In an embodiment, the pair of parallel support beams 129 completely surround the linear support member 150. An opening 153 at the proximal end 152 of the linear support member 150 lines up with the openings 129a. A protrusion 112 on a plastic mechanical tab 110 snaps into opening 129a and pivotally engages the linear support member 150 with the upper member 120. In an embodiment, the proximal end 152 of the linear support member 150 and the two parallel support beams 129 are pivotally engaged using the mechanical tab 110. In other embodiments, the engagement between the linear support member 150 and the upper member 120 can be accomplished using a rivet, a pin, or a nut/bolt combination. A lip 158 forms a shorter horizontal section of the body 154 having two sections protruding off of the lip 158. The angulation arm 157 and an elevation leg 155 both protrude from the lip 158 of the body 154. The angulation arm 157 passes through the opening 126 of the operating mechanism 128 of the hinge assembly 125 of the upper member 120 and is held in place with locking nut 166. The locking nut 166 engages the threads of the angulation arm 157 and locks at the opening 126 of the operating mechanism 128. Locking teeth 159 of the elevation leg 155 locks with the stop tab 137 on the outer surface 131 of the handle 134.

During a gynecological examination or surgical procedure, it is sometimes desirable to illuminate the working area so that a medical professional performing the procedure can properly view the working area. Typical specula are not equipped with illumination devices, and newer speculums that contain light sources generally generate unwanted heat, consume significant power, are tethered to a power source, and project light in unwanted directions. The power consumed requires wires to an external power supply which is cumbersome for a medical practitioner, creates a potential hazard to a patient, and is a source of cross-contamination, as the light source is not easily sterilized between procedures. The unwanted directionality of light will not only illuminate the practitioners working space, but also will illuminate the practitioner and impair the practitioner's vision.

Attempts to overcome the above shortcomings have been problematic themselves. One known speculum includes a fiber bundle built into the speculum and an external light source. While this overcomes the heat generation and light directionality problem, the problem for cross-contamination still exists. Another known speculum discloses a light bulb built into the speculum handle with a reflector also built into the handle. While this overcomes the problem of light directionality, the problem for cross-contamination and heat generation still exists. Other speculums disclose a battery operated halogen light source built into the handle. This solves the cross-contamination problem, but does not solve the light directionality problem and heat problem.

FIG. 10A, FIG. 10B, and FIG. 10C, show an embodiment of the built-in light source 160 that resides within the handle 134 of the disposable, plastic speculum 100. An outer housing 162 protects internal batteries 166, a light emitting diode (LED) 164, and internal components of a tab switch 165, which is removed to illuminate the LED 164 when illumination is desired. The LED 164 may produce any desired level of intensity. For example, a resistance tab on the built-in light source 160 may be used to control the intensity of light that the LED 164 can emit. The LED 164 has a high power efficiency and consumes relatively little electrical power with a long life time. The LED 164 solves the heat problem because the power efficiency of an LED is greatly superior to prior incandescent or laser solutions. The light output from the LED 164 is highly directional, emitting light only within an about twenty degree path. This narrow light path ensures that light is only projected onto the working area, and not directly into the practitioners vision. The LED 164 is energy efficient and can be powered by a single lightweight battery 166 or a number of batteries 166. Because the light source 160 is built-into the handle 134 of the disposable speculum 100, the problem of cross-contamination is eliminated. The built-in light source 160 also eliminates cumbersome and potentially dangerous wires extending from the speculum 100 to an external power supply.

In an embodiment, the LED light source 164 is a white LED. In an embodiment, single or multiple wavelength LED sources can be substituted to choose a light wavelength that is uniquely suited to materials, chemicals, tissue, or tools used in current or future gynecological procedures such that these materials, chemicals, tissue or tools will distinctly illuminate when such wavelengths are projected, thus aiding in the practitioners ability to view the procedure, perform the procedure, aid in material property changes (such as epoxy hardening or activating some other specific material property), alter the state of tissue life, or serving as a contamination neutralizing agent. In an embodiment, the LED light source 164 is a single wavelength light emitting diode. In an embodiment, the LED light source 164 is a multiple wavelength light emitting diode.

Figure 11:
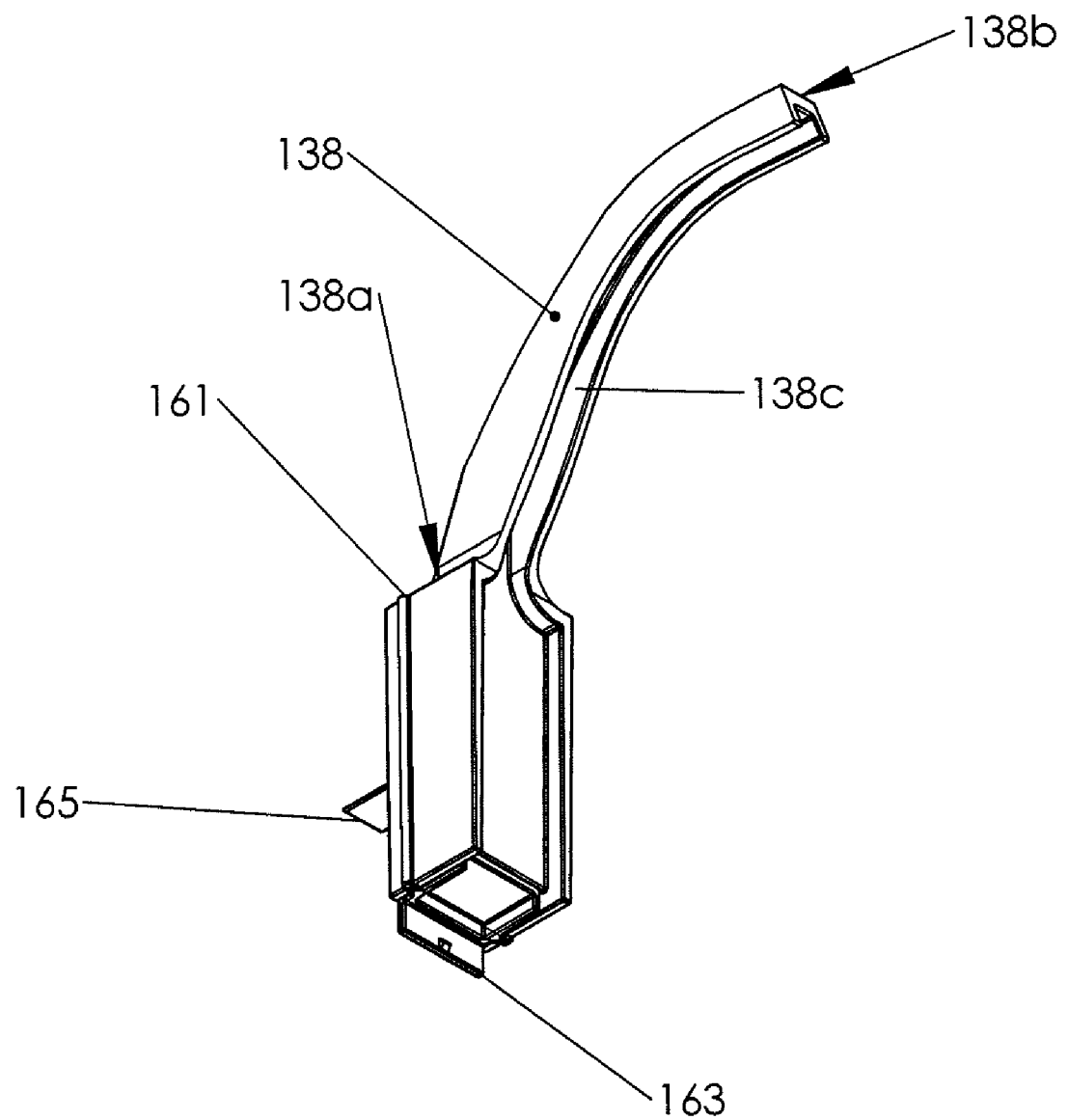
FIG. 11 shows an embodiment of a light guide and smoke evacuation channel for use with the vaginal speculum of FIG. 1A and FIG. 1B having the light source of FIG. 10A.

FIG. 11 shows an embodiment of the light guide 138 having a proximal end 138a and a distal end 138b. The light guide 138 runs from a distal end of the cavity 139 to a distal end of the lower blade 132 on the interior surface 133 of the lower blade 132. The proximal end 138a of the light guide 138 will transfer light coming from the light source 160 through the light guide 138 and out of the distal end 138b. The light guide 138 is contoured to ride on the interior surface 133 of the lower blade 132. The proximal end 138a of the light guide 138 may include a lens that couples with the light source 160 contained in the cavity 139 of the handle 134.

In certain gynecological procedures, it is desirable to remove abnormal cells from the internal and external portions of the cervix. Also, certain gynecological procedures use instruments that produce smoke, which makes it difficult for a medical professional to see a working space during the procedure. Therefore, the use of an external vacuum source during gynecological procedures is common. These external vacuum sources are cumbersome, difficult to manipulate during the procedure, and are a source of cross-contamination, since the vacuum is re-used for many patients.

Figure 12:
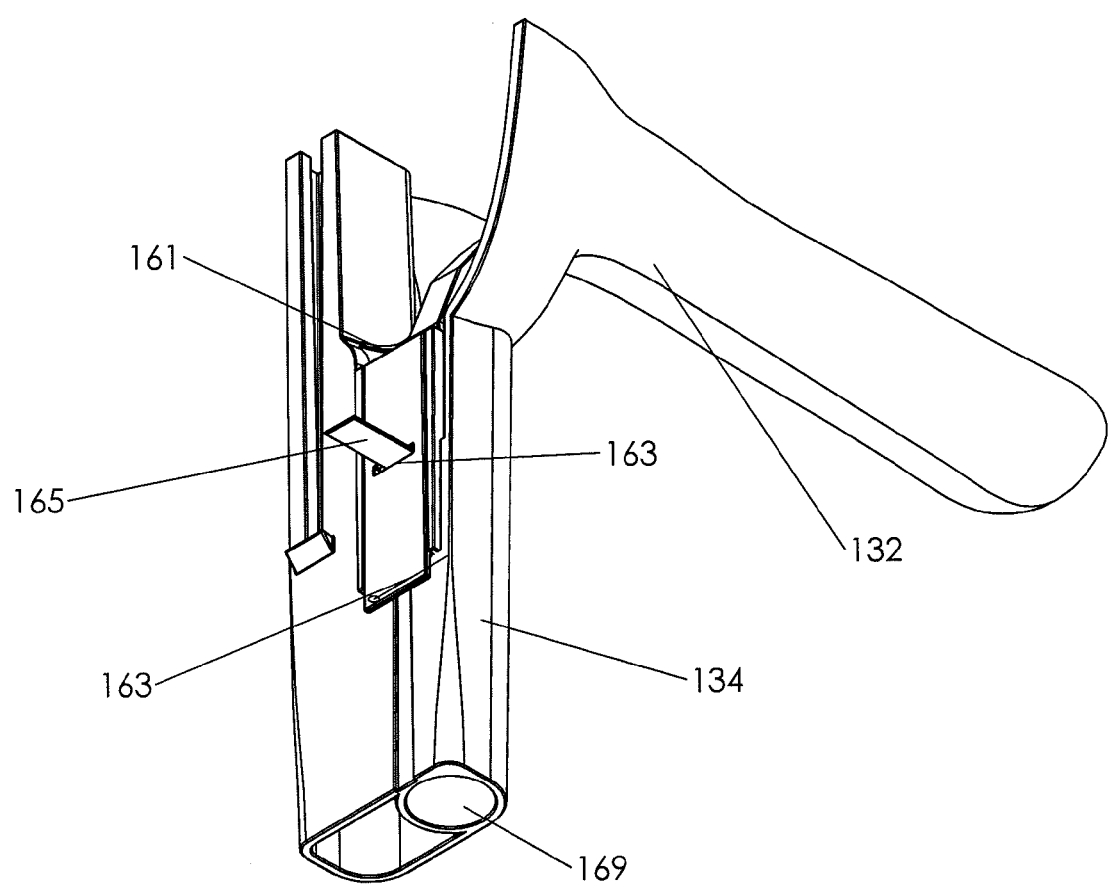
FIG. 12 shows a rear perspective view of the lower member of the vaginal speculum of FIG. 1 having the light source of FIG. 10A.

Existing speculum containing both a light guide and a smoke evacuation channel have typically built the light guide into the lower blade of the speculum and the smoke evacuation channel built into the upper blade of the speculum. This arrangement significantly detracts from the working space between the two blades that is needed to perform vaginal or uterine procedures. Additionally, an external suction tube must be connected to the upper blade of these existing speculum which further complicates and obstructs the working area for the physician. FIG. 11 in conjunction with FIG. 12 shows the lower member 130 of the speculum 100 having a smoke vacuum channel and a light guide merged together and positioned within the sunken relief 135 of the lower member 130 to create a compact structure. The combined smoke channel light guide consist of the light guide 138 with channel 138c for smoke evacuation cut into the side of the light guide 138 that comes in contact with the lower blade 132. A tunnel formed by the channel 138c is used as a smoke channel. The resulting compact structure created by merging the smoke vacuum channel and the light guide allows for the working space of the speculum 100 to be maximized. Additionally, an external suction tube may be connected to the handle of the speculum 100 at opening 169 instead of at the upper blade of the speculum 100. Connection of the external suction tube to the lower handle maintains a clear and unobstructed access to the vaginal area for the physician. Smoke is drawn from the distal end of the light guide 138b through the channel 138c that extends under the light guide and out the bottom of the speculum handle 134 where external suction tubing can be attached 169. In an embodiment, debris is drawn from the distal end of the light guide 138b through the channel 138c that extends under the light guide and out the bottom of the speculum handle 134 where external suction tubing can be attached 169. In an embodiment, bodily fluids are drawn from the distal end of the light guide 138b through the channel 138c that extends under the light guide and out the bottom of the speculum handle 134 where external suction tubing can be attached 169.

The ability of the speculum 100 of the present disclosure to withstand applied loads is a result of a combination of components of the speculum 100, including, but not limited to, the geometry of the hinge assembly 125, including the spaced apart distance 121 of the pair of parallel support beams 129, the geometry of the upper blade 122 and the lower blade 132, and the interdependent loading between the various components. In an embodiment, during use, pressure exerted on the operating mechanism 128 via the operating arm 127 is transferred to the hinge assembly 125, the mechanical tab 110, and down the elongated body 154 of the linear support member 150. As shown clearly in FIG. 3 and FIG. 8, the operating mechanism 128 is an extension of the hinge assembly 125, extending outwards and downwards at an angle. This extension design of the operating mechanism 128 imparts favorable loads on the plastic linear support member 150. For example, the operating mechanism 128 is capable of absorbing some of the initial load that a user imparts on the speculum 100, such that a reduced load is felt at the linear support member 150. The load placed on the linear support member 150 is directed in a downward direction. This in turn results in a reduced load down the elongated body 156 of the linear support member 150. In an embodiment, the load placed on the elongated body 156 of the linear support member 150 is about ½ that of the initial load supplied to the operating mechanism 128 when the speculum 100 is in a fully opened state. This reduction in load at the linear support member 150 reduces the tendency of the linear support member 150 to buckle and permits the use of a plastic linear support member 150.

During use of the speculum 100, for example during a gynecological procedure, the speculum 100 is inserted into a patient's vagina. The vaginal walls in turn exert a pressure, or load, on the upper blade 122 and the lower blade 132 of the speculum 100. The upper blade 122 and the lower blade 132 are capable of transferring this load to the support member 150 and the operating mechanism 128 because of the unique design of the hinge assembly 125 of the upper member 120 of the speculum 100. The pair of parallel support beams 129 are capable of supporting the load in compression and distributing the load equally down both the linear support member 150 and the operating mechanism 128. This results in a great deal of holding power in a relatively small area. The two parallel support beams 129 provide an effective load transfer to the inclined surface of the operating mechanism 128. The two parallel support beams 129 are loaded in compression and buckling is prevented due to the presence of the linear support member 150 at an inside face of the hinge assembly 125 and the flanges of the plastic mechanical tab 110 on the outside face.

The upper blade 122 and the lower blade 132 have a curved shape which increases the stiffness and strength of the blades. The stiffness imparted on the curved blades enables the blades to support the applied load along an entire length of the blades, without the need for additional strengthening structures within the blades. The proximal end 152 of the linear support member 150 and the two parallel support beams 129 help prevent failure of the speculum 100 due to asymmetric loading on the blades that would cause the speculum 100 to twist relative to the handle's 134 axis. The design of the speculum 100 prevents twisting by loading the linear support member 150 in torsion.

To operate the speculum 100 of the present disclosure during a gynecological procedure, the upper blade 122 and the lower blade 132 are inserted into a vagina of a patient in a closed position. Closed position can refer to complete closure, where the upper blade 122 engages the lower blade 132, or can refer to partial closure, where the upper blade 122 and the lower blade 132 are partially separated. Thereupon, the linear support member 150 is moved upwardly by pressing on the elevation leg 155 until a desired degree of opening has been attained. The locking teeth 159 of the elevation leg 155 locks with the stop tab 137 on the outer surface 131 of the handle 134. In an embodiment, when the desired degree of opening has been attained, the operating arm 127 of the operating mechanism 128 is pressed spreading the upper blade 122 and the lower blade 132 apart at an angle. The locking nut 166 on the angulation arm 157 locks at the opening 126 of the operating mechanism 128, resulting in the speculum 100 being held in the open position. The light source 160 may be turned on to illuminate a surgical or examination site. The pull tab 165 of the light source 160 is removed, resulting in the LED 164 illuminating. At the end of the procedure, the pull tab 165 is inserted again to turn the LED 164 off.

It is to be understood that a speculum 100 of the present disclosure may be fabricated in various sizes, such that the proper sized speculum 100 can be used for each patient. The speculum 100 may also be fabricated from various strength plastic materials based on the desired use of the speculum 100, as long as the structural integrity of the speculum 100 remains. For example, for a routine PAP test, a lower strength speculum 100 may be used as compared to a speculum 100 for use during vaginal hysterectomy.

In an embodiment, a speculum 100 is provided that includes an adjustable upper blade 122 and an adjustable lower blade 132 capable of expanding during use of the speculum 100. Means for providing adjustable blades include, but are not limited to, the use of laterally adjusting blades that expand the width of the blades and the use of longitudinally adjustable blades that expand the length of the blades. The adjustable blades can be withdrawn partially or completely.

In an embodiment, a speculum 100 is provided that includes heating means for warming the upper blade 122 or the lower blade 132. The extra warmth provided by the heating means enhances patient comfort and helps to relax the vaginal area. Means for heating the blades include, but are not limited to, the use of heating coils within a hollowed out space of the blades, the use of powdered chemicals within a hollowed out space of the blades that are able to oxidize when exposed to air. In an embodiment, a speculum 100 includes heating coils on the upper blade 122 and the lower blade 132 for bringing the temperature of the blades to body temperature. In an embodiment, the heating coils can be powered by the batteries 166 used in the built-in light source 160. In an embodiment, the heating coils can be powered by a different battery.

In an embodiment, a speculum 100 is provided that includes a distally mounted camera chip for real-time data capture and/or viewing of a medical procedure. The camera chip can store and/or capture data, and communicate with computer software to analyze the data. Data captured on the camera chip can be analyzed for cellular and visual abnormalities of the vulva, vagina and cervix.

In an embodiment, a speculum 100 is provided that includes a pressure gauge, so that the pressure being applied from the speculum 100 to the vagina, or from the vagina to the speculum 100, can be monitored, as well as the tightness of the vaginal canal. The pressure gauge may be similar to a strain gauge and may be built into the speculum 100, for example, at the hinge assembly 125.

In an embodiment, a speculum 100 is provided that includes a pH test strip or a pH meter, for the fast and accurate determination of the acidity level of the vaginal canal being examined. The pH strip or pH meter would be exposed to vaginal secretions to access the pH at any point in a gynecological or surgical procedure.

In an embodiment, a speculum 100 is provided that includes means for lubricating one of the upper blade 122 or the lower blade 132. The lubricated blades makes it easy for the speculum 100 to be inserted into a vaginal cavity of a patient, while providing a moist work environment during a gynecological or surgical procedure. In an embodiment, a body of the upper blade 122 and/or the lower blade 132, has a hollowed-out space for passage of a lubricating jelly, as well as holes at a surface for release of the lubricating jelly. In an embodiment, the speculum 100 may come pre-packaged with an amount of lubricating jelly within the hollowed-out space of the blade. The lubricating jelly is released through the holes present at the blades surface, for example, by pushing a button on the handle 134. In an embodiment, the speculum 100 may include a port that can attach to a luer-lock syringe having the lubricating jelly, for passage of the lubricating jelly into the blades.

A method for dilating a vagina includes providing a disposable vaginal speculum, the speculum having an upper member having an upper blade; a support structure including a pair of parallel pieces spaced a distance apart that extend downward from an interior side of the upper blade; an operating mechanism extending off from the support structure and including an operating arm, the operating mechanism positioned at a single side of the upper blade; a lower member having a lower blade; and a linear support member having a proximal end, a distal end, and an elongated body therebetween, the linear support member vertically moveable within a track positioned at a single side of a handle portion of the lower member; inserting the upper blade and the lower blade of the speculum into an opening of the vagina; and creating a working space between the upper blade and the lower blade, thus dilating the vagina.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A speculum comprising:
   a. an upper member comprising
      (1) an upper blade having a proximal end, a distal end, a left side and a right side when viewed from the proximal end, and an interior surface,
      (2) a hinge assembly positioned at one side of the upper blade, the hinge assembly comprising at least two parallel hinge support pieces which extend downward from the interior surface of the upper blade and which define a space therebetween that has an opening, and
      (3) an operating arm, wherein the hinge assembly does not extend laterally beyond the most lateral edge of the operating arm;
   b. a lower member comprising
      (1) a lower blade having a proximal end, a distal end, a left side and a right side when viewed from the proximal end, and an interior surface, and
      (2) a handle portion defining a vertical track and further defining a cavity; and
   c. a linear support member having a proximal end, a distal end, and an elongated body therebetween,
   wherein the proximal end of the linear support member is hingedly positioned within the space defined by the hinge support pieces of the upper member, and wherein the elongated body of the linear support member is vertically moveable within the vertical track of the lower member that is positioned at the side of a handle portion.

2. The speculum of claim 1 wherein the opening of the hinge assembly and the track are aligned.

3. The speculum of claim 1 wherein the handle portion further comprises an internally powered light source.

4. The speculum of claim 3 wherein at least a portion of the interior surface of the lower blade includes a light guide for directing light from the light source to the distal end of the lower blade.

5. The speculum of claim 1 wherein at least a portion of the interior surface of the lower blade includes a channel for removing smoke.

6. The speculum of claim 1 wherein at least a portion of the interior surface of the lower blade includes a light guide and a suction vacuum channel merged together to create a compact structure.

7. The speculum of claim 1 wherein the linear support member, the hinge assembly, the upper blade, and the lower member are fabricated from one or more plastics or plastic composites.

8. The speculum of claim 7 wherein the linear support member, the hinge assembly, the upper blade, and the lower member are fabricated for single-use and are disposable.

9. A speculum comprising:
   an upper member having an upper blade and a hinge assembly positioned at one side of the upper blade, the hinge assembly comprising at least two parallel hinge support pieces which extend downward from the interior surface of the upper blade and which define a space therebetween that has an opening;
   a lower member having a handle portion and a lower blade, wherein a combined smoke channel and light guide directs light from a light source in the handle to a distal end of the lower blade; and
   a linear support member having a proximal end, a distal end, and an elongated body therebetween, wherein the proximal end of the linear support member is hingedly positioned within the space defined by the hinge support pieces of the upper member, and the linear support member is vertically moveable within a track positioned in the lower member.

10. The speculum of claim 9 wherein the linear support member pivotally engages the hinge assembly of the upper member.

11. The speculum of claim 9 wherein the proximal end of the linear support member engages at least one of a pair of spaced apart parallel pieces of the hinge assembly.

12. The speculum of claim 9 wherein the hinge assembly and the track are positioned at a same side of the speculum.

13. The speculum of claim 9 wherein the elongated body of the linear support member further includes an angulation arm and an elevation leg.

14. The speculum of claim 9 wherein the linear support member, the hinge assembly, the upper blade, and the lower member are fabricated from one or more plastics or plastic composites.

15. The speculum of claim 9 wherein the linear support member, the hinge assembly, the upper blade, and the lower member are fabricated for single-use and are disposable.

16. The speculum of claim 15 wherein removal of an electrically isolating tab in the light source activates the light source.

17. The speculum of claim 9 wherein the handle portion includes an internally powered light source.

18. A method for dilating a vagina comprising:
   providing a disposable vaginal speculum, the speculum having an upper member having an upper blade that has an interior surface; a hinge and support structure including a pair of parallel pieces spaced a distance apart that extend downward from an interior surface of the upper blade; an operating mechanism extending off from the support structure and including an operating arm, the operating mechanism positioned at a single side of the upper blade; wherein the hinge does not extend laterally beyond the most lateral edge of the operating mechanism, a lower member having a lower blade; and a linear support member having a proximal end, a distal end, and an elongated body therebetween, the linear support member vertically moveable within a track positioned at a single side of a handle portion of the lower member;

inserting the juxtaposed upper blade and the lower blade of the speculum into the vaginal opening; and creating a working space between the upper blade and the lower blade, thus dilating the vagina.

19. The method of claim 18 wherein the step of creating the working space between the upper blade and the lower blade comprises at least one of the steps of moving the linear support member of the speculum in an upward direction within the track of the lower member, spreading the upper blade and the lower blade apart at an angle by pressing on the operating arm of the operating mechanism, or a combination thereof; and obtaining a desired degree of opening between the upper blade and the lower blade, thereby creating a working space.

20. The method of claim 18 further comprising the step of activating a light source disposed in the handle portion of the lower member to illuminate the working space.

* * * * *